US011779772B2

(12) United States Patent
Lim et al.

(10) Patent No.: US 11,779,772 B2
(45) Date of Patent: Oct. 10, 2023

(54) ALL METAL ENCLOSED IMPLANTABLE MEDICAL DEVICE WITH EXTERNAL BLE ANTENNA FOR RF TELEMETRY

(71) Applicant: Pacesetter, Inc., Sylmar, CA (US)

(72) Inventors: Wisit Lim, Santa Clarita, CA (US); Perry Li, Arcadia, CA (US)

(73) Assignee: Pacesetter, Inc., Sylmar, CA (US)

( * ) Notice: Subject to any disclaimer, the term of this patent is extended or adjusted under 35 U.S.C. 154(b) by 240 days.

(21) Appl. No.: 17/324,393

(22) Filed: May 19, 2021

(65) Prior Publication Data

US 2021/0268295 A1     Sep. 2, 2021

Related U.S. Application Data

(62) Division of application No. 15/943,500, filed on Apr. 2, 2018, now Pat. No. 11,040,210.

(51) Int. Cl.
| | | |
|---|---|---|
| *A61N 1/372* | (2006.01) | |
| *A61N 1/375* | (2006.01) | |
| *A61B 5/00* | (2006.01) | |
| *H01Q 1/22* | (2006.01) | |

(52) U.S. Cl.
CPC ....... *A61N 1/37229* (2013.01); *A61N 1/3754* (2013.01); *A61B 5/0031* (2013.01); *A61N 1/37512* (2017.08); *H01Q 1/22* (2013.01); *Y10T 29/49117* (2015.01)

(58) Field of Classification Search
CPC ............ A61N 1/37229; A61N 1/37223; A61N 1/3752; A61N 1/37512; A61N 1/3754; A61N 1/3758; A61N 1/375; H01Q 1/273; A61B 5/0031; Y10T 29/49016; Y10T 29/49117

USPC .................. 29/825, 829, 832, 854, 856, 876
See application file for complete search history.

(56) References Cited

U.S. PATENT DOCUMENTS

| | | | |
|---|---|---|---|
| 5,324,311 | A | 6/1994 | Acken |
| 5,522,861 | A | 6/1996 | Sikorski et al. |
| 6,205,358 | B1 | 3/2001 | Haeg et al. |
| 6,763,269 | B2 | 7/2004 | Cox |
| 6,766,200 | B2 | 7/2004 | Cox |
| 6,809,701 | B2 | 10/2004 | Amundson et al. |

(Continued)

OTHER PUBLICATIONS

Restriction Requirement dated Jan. 10, 2020, U.S. Appl. No. 15/943,500, filed Apr. 2, 2018.

(Continued)

*Primary Examiner* — Thiem D Phan
(74) *Attorney, Agent, or Firm* — Vierra Magen Marcus LLP

(57) ABSTRACT

An implantable medical device including a can, a feedthrough and an antenna assembly. The can includes a lead connector assembly, electronics, and a metal wall defining a hermetic sealed compartment. The electronics and lead connector assembly are located in the hermetic sealed compartment. The feedthrough extends through the metal wall between the hermetic sealed compartment and exterior the metal wall. The antenna assembly includes an antenna extending along the metal wall in a spaced-apart manner from the metal wall and encased in a dielectric material. The dielectric material occupies a space between the antenna and the metal wall. The antenna is electrically connected to the electronics via an RF conductor of the feedthrough.

18 Claims, 10 Drawing Sheets

(56) References Cited

U.S. PATENT DOCUMENTS

| | | | |
|---|---|---|---|
| 7,046,499 B1 | 5/2006 | Imani et al. | |
| 7,047,076 B1 * | 5/2006 | Li | A61N 1/37229 343/718 |
| 7,164,950 B2 | 1/2007 | Kroll et al. | |
| 7,174,212 B1 | 2/2007 | Klehn et al. | |
| 7,225,029 B2 | 5/2007 | Shankar et al. | |
| 7,616,991 B2 | 11/2009 | Mann et al. | |
| 7,903,043 B2 | 3/2011 | Rawat et al. | |
| 8,155,743 B2 | 4/2012 | Rundle et al. | |
| 8,600,500 B1 | 12/2013 | Rosenberg et al. | |
| 10,176,412 B2 * | 1/2019 | Geissler | G06K 19/04 |
| 11,040,210 B2 | 6/2021 | Lim et al. | |
| 2004/0215280 A1 | 10/2004 | Dublin et al. | |
| 2005/0222633 A1 | 10/2005 | Edvardsson | |
| 2006/0267843 A1 | 11/2006 | Sakama et al. | |
| 2007/0134974 A1 | 6/2007 | Starke et al. | |
| 2009/0163979 A1 | 6/2009 | Hjelm et al. | |
| 2009/0248112 A1 | 10/2009 | Mumbru et al. | |
| 2010/0030296 A1 | 2/2010 | Rundle et al. | |
| 2010/0082080 A1 | 4/2010 | Mateychuk | |
| 2010/0109958 A1 | 5/2010 | Haubrich et al. | |
| 2010/0114245 A1 | 5/2010 | Yamamoto et al. | |
| 2010/0114247 A1 | 5/2010 | Snitting | |
| 2010/0161002 A1 | 6/2010 | Aghassian et al. | |
| 2010/0168817 A1 | 7/2010 | Yamamoto et al. | |
| 2010/0168818 A1 | 7/2010 | Barror et al. | |
| 2010/0194541 A1 | 8/2010 | Stevenson et al. | |
| 2012/0130206 A1 | 5/2012 | Vajha et al. | |
| 2012/0194981 A1 | 8/2012 | Kempf et al. | |
| 2012/0200011 A1 | 8/2012 | Pavlovic | |
| 2012/0283806 A1 | 11/2012 | Troosters et al. | |
| 2014/0168917 A1 | 6/2014 | Marzano et al. | |
| 2014/0275916 A1 | 9/2014 | Nabutovsky et al. | |
| 2014/0295688 A1 | 10/2014 | Deininger et al. | |
| 2014/0364714 A1 | 12/2014 | Ameri et al. | |
| 2015/0255858 A1 | 9/2015 | Li et al. | |
| 2016/0331980 A1 | 11/2016 | Strommer et al. | |
| 2017/0266451 A1 | 9/2017 | Lim et al. | |
| 2018/0050214 A1 | 2/2018 | Rump | |

OTHER PUBLICATIONS

Response to Restriction dated Mar. 10, 2020, U.S. Appl. No. 15/943,500, filed Apr. 2, 2018.

Non-final Office Action dated Apr. 23, 2020, U.S. Appl. No. 15/943,500, filed Apr. 2, 2018.

Response to Office Action dated Jun. 15, 2020, U.S. Appl. No. 15/943,500, filed Apr. 2, 2018.

Final Office Action dated Sep. 30, 2020, U.S. Appl. No. 15/943,500, filed Apr. 2, 2018.

Response to Office Action dated Nov. 25, 2020, U.S. Appl. No. 15/943,500, filed Apr. 2, 2018.

Advisory Action dated Dec. 7, 2020, U.S. Appl. No. 15/943,500, filed Apr. 2, 2018.

Notice of Allowance dated Mar. 22, 2021, U.S. Appl. No. 15/943,500, filed Apr. 2, 2018.

* cited by examiner

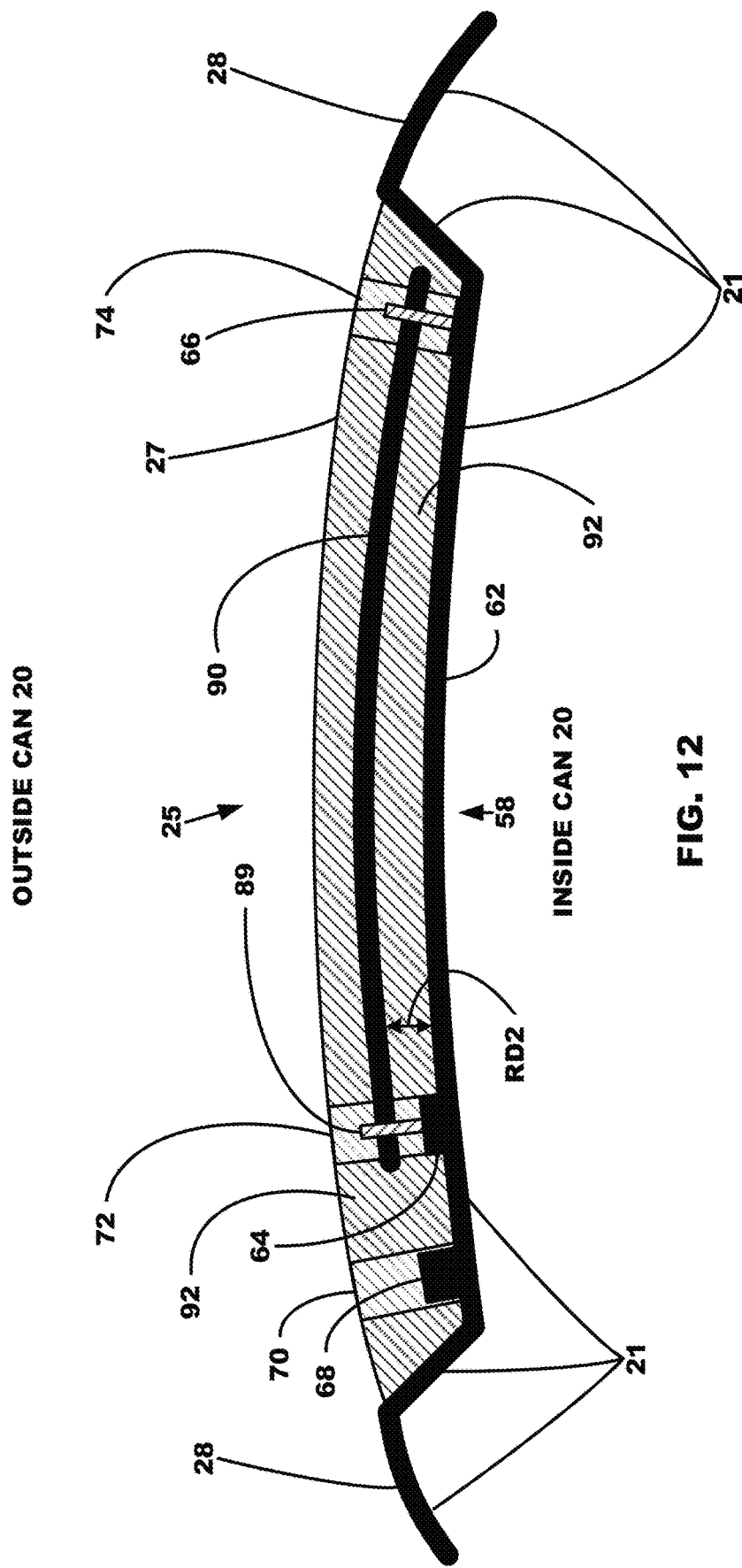

ALL METAL ENCLOSED IMPLANTABLE MEDICAL DEVICE WITH EXTERNAL BLE ANTENNA FOR RF TELEMETRY

CROSS-REFERENCE TO RELATED APPLICATIONS

The present application is a divisional application of U.S. application Ser. No. 15/943,500 filed Apr. 2, 2018, issued as U.S. Pat. No. 11,040,210 on Jun. 22, 2021, which is hereby incorporated by reference in its entirety.

FIELD OF THE INVENTION

Aspects of the present invention relate to medical apparatus and methods. More specifically, the present invention relates to systems and methods for implementing an all metal enclosed implantable medical device with external BLE antenna for RF telemetry.

BACKGROUND OF THE INVENTION

Implantable pulse generators (IPGs) come in a variety of forms for different applications. For example, some IPGs, such as pacemakers and implantable cardioverter defibrillators (ICDs), are used in the treatment of cardiac conditions. Other IPGs, such as neuromodulators or neurostimulators, are used in chronic pain management or the actuation and control of other body systems. These devices, which are known as implantable medical devices (IMDs), commonly include a housing (i.e., can), feedthroughs, and a connector assembly that is enclosed in a header. Electrical stimulation originating in the housing is led to the connector assembly through the feedthroughs. The connector assembly serves to transmit electrical signals out of the IMD and to a lead electrically connected to the connector assembly, the lead transmitting electrical signals between the IMD and patient tissue.

Typically, existing IMDs include a metal case (i.e., housing or can) and a traditional separate epoxy or tecothane header attached to the metal case. The metal case encloses the electronic components of the IMD, and the traditional header encloses the lead connector blocks and the communication antenna, which may be for inductive telemetry or RF. The antenna allows the IMD to communicate with an external unit while the IMD is implanted in the patient.

Fabrication of connector blocks and antennas inside traditional headers is difficult and incurs a high cost. There have been designs of all metal enclosed IMDs eliminating the requirement of a traditional separate header in the past. However, the downside of these previous all metal enclosed IMDs is that they only work with inductive telemetry as placement of the RF antenna in an all metal enclosed IMD effectively shields all RF communication.

Unfortunately, and unlike the more advantageous RF communication, an inductive interface requires a relatively short distance (on the order of centimeters) between the IMD and the extracorporeal unit with which it communicates. This, in turn, may be inconvenient for the patient as well as impractical for the personnel conducting the procedure. Moreover, the maximum data rate for an inductive interface is relatively low as compared to RF, which results in practical limitations as to the amount of data that can be communicated.

Some IMDs with traditional headers use the MICS (Medical Implant Communication Service) frequency band of 402-405 MHz. At this frequency, antennas need to be relatively large compared to the size of the header in order to function well. This has led to the widespread use of wire type antennas such as the monopole (open loop), closed loop, or inverted F. These antennas have proven to be very versatile with their ability to conform to the shape of the header and route around bore holes and lead connectors of the traditional headers. However, this means that any changes to an existing or new header on the IMD can lead to significant or complete redesigns of the antenna. Also, header sizes are substantial in height to accommodate these antennas, thereby making the overall IMD large.

Therefore, there is a need in the art for an all metal enclosed IMD capable of RF (BLE) telemetry communication.

SUMMARY

The communication arrangements and methods disclosed herein allow for an all metal enclosed implantable medical device having an external BLE antenna for RF telemetry.

In one embodiment, the implantable medical device includes a can, a feedthrough and an antenna assembly. The can includes a lead connector assembly, electronics, and a metal wall defining a hermetic sealed compartment. The electronics and lead connector assembly are located in the hermetic sealed compartment. The feedthrough extends through the metal wall between the hermetic sealed compartment and exterior the metal wall. The antenna assembly includes an antenna extending along the metal wall in a spaced-apart manner from the metal wall and encased in a dielectric material. The dielectric material occupies a space between the antenna and the metal wall. The antenna is electrically connected to the electronics via an RF conductor of the feedthrough.

The antenna may use the metal wall as a ground plate, and the antenna may communicate in a Bluetooth frequency band contained within 2.40 to 2.48 GHz.

The implantable medical device may further include a case connection pin electrically connecting the antenna and the metal wall. In such an embodiment, the case connection pin and the RF conductor may have electrical connections with the antenna at generally opposite areas of the antenna. Also, the antenna and the spaced-apart metal wall may have generally matching arcuate configurations such that spacing between the antenna and metal wall is generally consistent along the length of the antenna.

The implantable medical device may further include an anchor coupling the antenna assembly to the metal wall. In such an embodiment, the case connection pin and anchor may be at opposite ends of the antenna assembly. Also, the RF conductor may be located between the case connection pin and the anchor. However, regardless of the arrangement of the case connection pin, RF conductor, and anchor relative to each other and the antenna assembly and metal wall for such embodiments, while the anchor couples to the antenna assembly, the anchor does not connect to the antenna itself; only the RF conductor and case connection pin connect with the antenna itself.

In one embodiment of the device, the antenna may have an end-to-end length of between approximately 0.7" and approximately 0.75", a side-to-side width of between approximately 0.06" and approximately 0.1", and a thickness of between approximately 0.015" and approximately 0.03". The antenna assembly may have an end-to-end length of between approximately 0.9" and approximately 1", a side-to-side width of between approximately 0.1" and approximately 0.15", and a thickness of between approximately 0.04" and approximately 0.1".

In one embodiment of the device, a top surface of the antenna may be recessed below a top surface of the antenna assembly between approximately 0.01" and approximately 0.03". The metal wall may be spaced-apart from a bottom surface of the antenna by between approximately 0.02" and approximately 0.04".

In one embodiment of the device, the dielectric material includes at least one of a thermosetting polymer, an epoxy, thermoplastic, polyurethane, tecothane, pellethane, silicone, acrylic, bionate, or ceramic.

In one embodiment, a method of manufacturing an implantable medical device includes electrically connecting an antenna to a metal wall via an RF conductor of a feedthrough. The metal wall defines a hermetic sealed compartment in which electronics and a lead connector assembly are located. The antenna extends along the metal wall in a spaced-apart manner. The antenna is encased in a dielectric material that fills a space between the antenna and the metal wall. The RF conductor is in electrical communication with the electronics.

In one embodiment of the method, the dielectric material includes at least one of a thermosetting polymer, an epoxy, thermoplastic, polyurethane, tecothane, pellethane, silicone, acrylic, bionate, or ceramic In one embodiment of the method, the dielectric material and the antenna encased therein form an antenna assembly, which is applied as a unit to the metal wall when the antenna is electrically connected to the metal wall. However, in another embodiment, the dielectric material is applied about the antenna subsequent to the antenna being electrically connected to the wall.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

FIG. 12 is the same view of the antenna assembly of FIG. 9, except with the antenna assembly fully mounted on, and secured to, the all metal hermetic sealed wall of the can.

DETAILED DESCRIPTION

Figure 1:
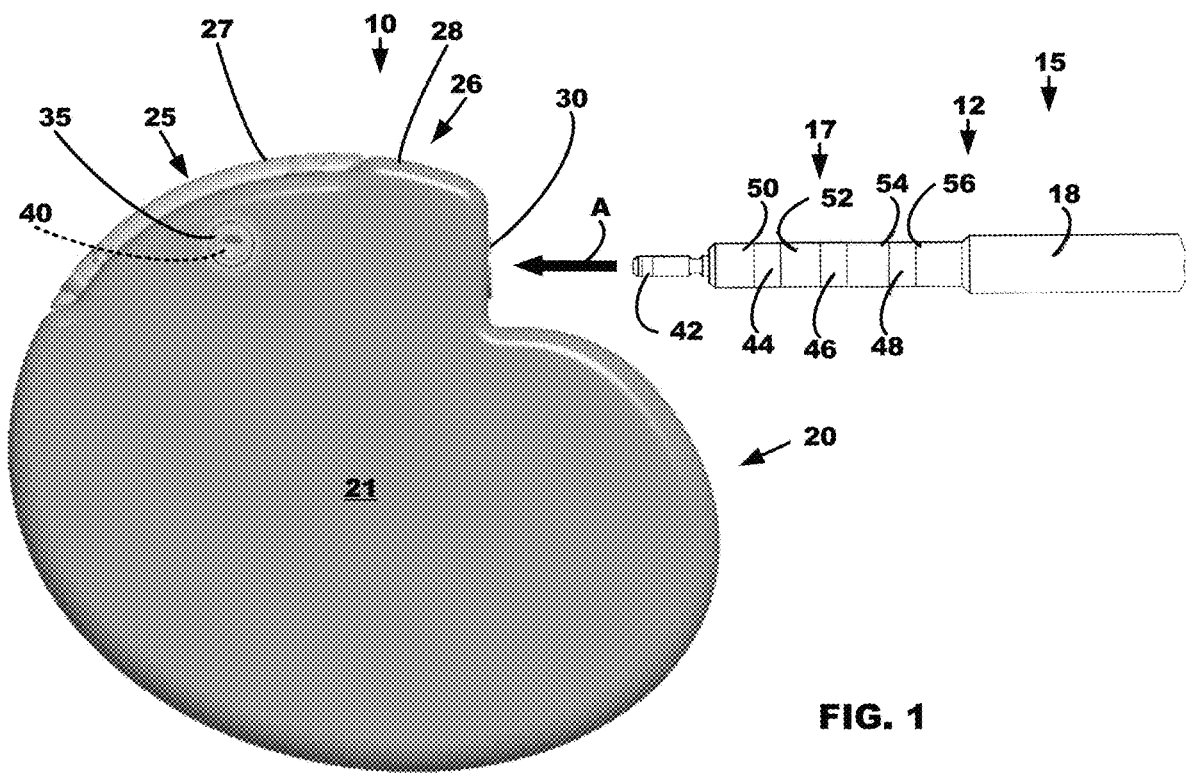
FIG. 1 is a side view of an IMD and a proximal end of an implantable medical lead.

The following discussion is directed to an all metal enclosed implantable medical device (IMD) 10 having an external BLE antenna 90 for RF telemetry. As one non-limiting example, and as discussed in greater detail below, the IMD 10 may include a can 20, a feedthrough 64 and an antenna assembly 25. The can 20 includes a lead connector assembly 32, electronics (e.g., a battery 78, hybrid 80, flex connector 82, etc.), and a metal wall 21 defining a hermetic sealed compartment. The electronics and lead connector assembly are located in the hermetic sealed compartment. The feedthrough extends through the metal wall between the hermetic sealed compartment and exterior the metal wall. The antenna assembly 25 includes an antenna 90 extending along the metal wall 21 in a spaced-apart manner from the metal wall and encased in a dielectric material 92. The dielectric material 92 occupies a space between the antenna 90 and the metal wall 21. The antenna is electrically connected to the electronics via an RF conductor 89 of the feedthrough. This IMD advantageously provides an all metal enclosed electronics package that is still capable of RF telemetry.

Figure 2:
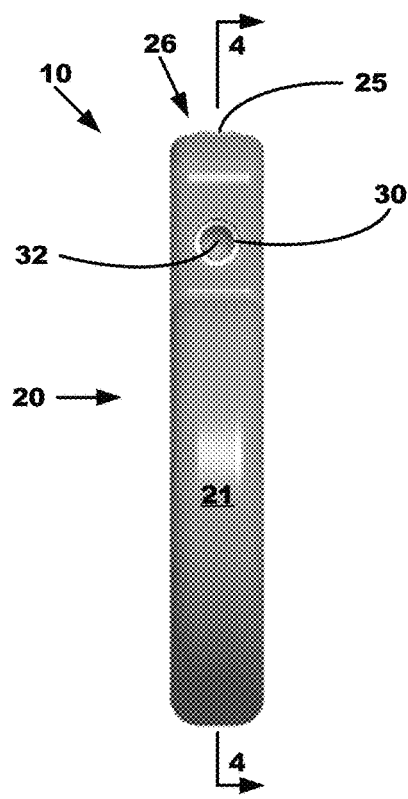
FIG. 2 is an end view of the IMD of FIG. 1.

FIG. 1 is a side view of an IMD 10 and a proximal end 12 of an implantable medical lead 15, and FIG. 2 is an end view of the IMD 10. As shown in FIGS. 1 and 2, the IMD 10 includes an all metal enclosed hermetic sealed electronics component 20 of the IMD 10, which may be referred to herein for purposes of this discussion as a housing or can 20, and an antenna assembly 25 secured to an arcuate upper region 26 of the can 20. The antenna assembly 25 has an arcuate upper surface 27 that complements an arcuate upper surface 28 of the arcuate upper region 26 of the can 20 to provide a smooth and non-obtrusive transition between the upper surfaces 27, 28. The can 20 further includes an exterior opening 30 of a lead connector assembly 32 and a septum 35 covering a setscrew 40. As discussed in greater detail below, the housing or can 20 includes an all metal wall 21 that encloses in a hermetic sealed compartment within the can 20 essentially all electronic components of the IMD 10 less the exterior antenna assembly 25. Because the antenna assembly 25 is located on the exterior of the wall 21 of the can 20, the antenna assembly 25 can support RF/BLE telemetry for the IMD 10.

The proximal end 12 of the implantable medical lead 15 includes a lead connector end 17 that extends proximally from a lead body 18. The lead connector end includes electrical contacts in the form of a proximal pin contact 42 and three ring contacts 44, 46, 48 distal the pin contact. The contacts are electrically insulated from each other by electrical insulating rings 50, 52, 54, 56.

As indicated by arrow A in FIG. 1, the lead connector end 17 enters the exterior opening 30 to be plugged into the lead connector assembly 32. In doing so, the electrical contacts 42, 44, 46, 48 electrically couple with corresponding electrical contacts of the lead connector assembly 32, and the electrical insulating rings 50, 52, 54, 56 form a fluid-tight seal arrangement with O-ring type seals (not shown) within the lead connector assembly 32. While an IS-4 connector is illustrated in FIG. 1, it should be understood that the teachings herein are applicable to connector assemblies of all types, including IS-1, DF-1, DF-4, etc., and the IS-4 connector assembly depicted in FIG. 1 is merely for general discussion purposes.

Although not reflected in FIG. 1 due to the truncated depiction of the lead body illustrated therein, as known in the art, the lead body extends distally from the lead connector end a substantial distance. Electrical conductors, for example, cables, wires, coils, filars, or etc. (not shown) extend through the lead body from each electrical contact to a respective electrode supported on the lead body near its distal end. Thus, when the lead connector end 17 is plugged into the lead connector assembly 32 and electrical contact is thereby established between the contacts of the lead connector end and the contacts of the lead connector assembly, electrical signals may be communicated along the electrical conductors between the IMD and the electrodes.

Where the IMD is employed for administering electrotherapy to the heart, the electrodes supported on the lead body 18 near its distal end will take the form of sensing and pacing electrodes (not shown), and in some embodiments, defibrillation coils (not shown). Where the IMD is employed for chronic pain management, the electrodes supported on the lead body 18 near its distal end will take the form of the electrical stimulation electrodes (not shown).

Figure 3:
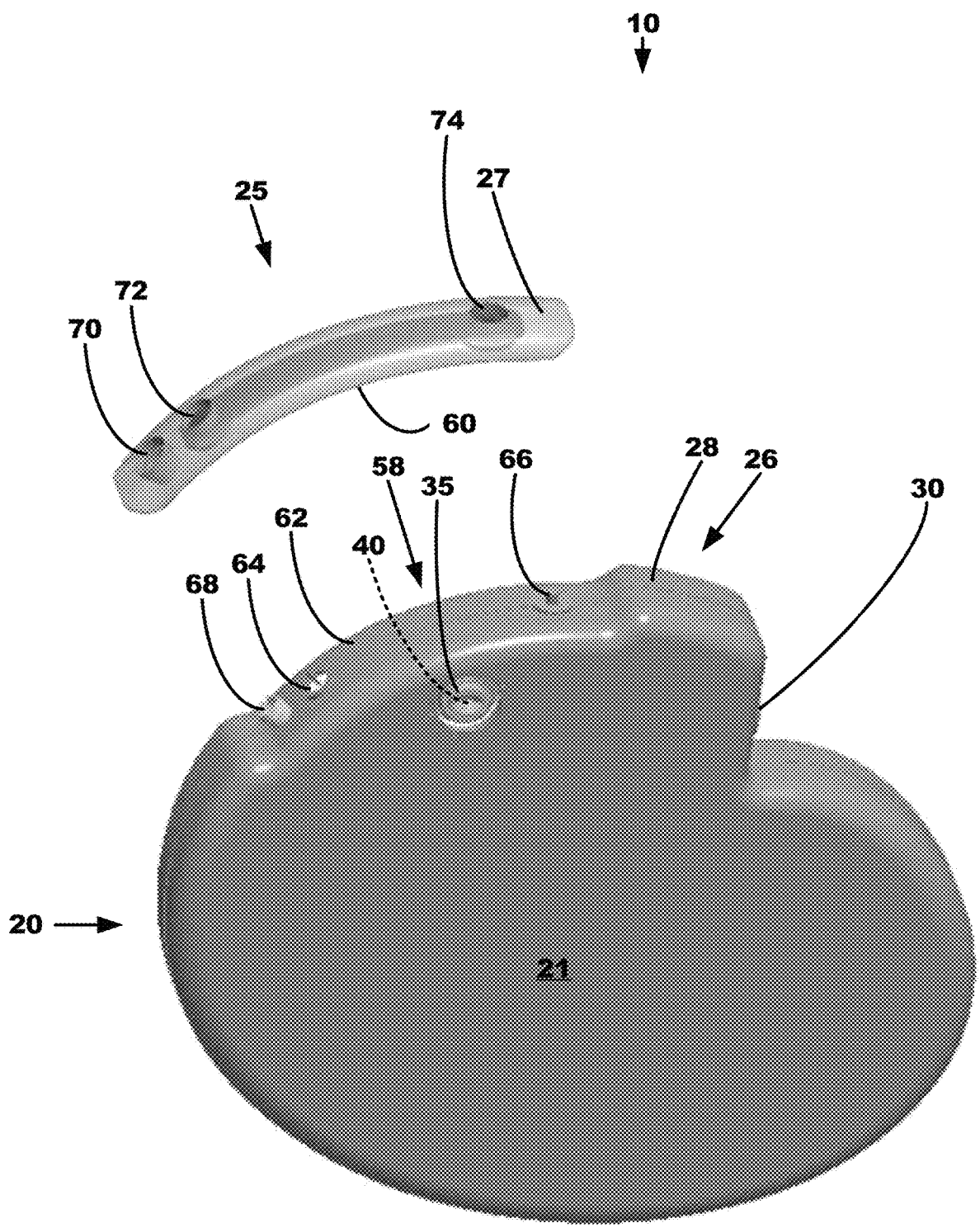
FIG. 3 is an exploded isometric view of the IMD showing its antenna assembly separate from the all metal enclosed hermetic sealed can that contains the connector assembly and electronic components of the IMD.

As can be understood from FIG. 3, which is an exploded isometric view of the IMD 10, the antenna assembly 25 is a separate component from the all metal enclosed hermetic sealed can 20 that contains the connector assembly 32 and electronic components of the IMD within the hermetic sealed all metal wall 21 of the can 20. A comparison of FIGS. 1 and 3 reveals that the antenna assembly 25 nests in a recessed outer region 58 of the can 20 when coupled with the can 20, the bottom mating surface 60 of the antenna assembly 25 having a complementary negative arcuate shape of an upper arcuate mating surface 62 of the recessed region of the can 20.

As shown in FIG. 3, the upper arcuate mating surface 62 includes an antenna feedthrough 64, a case connection pin 66, and an anchor assembly 68. The antenna assembly 25 includes an anchor hole 70, a feedthrough pin hole 72, and a connection hole 74. As discussed below in more detail, the antenna assembly 25 is secured to the recessed outer region 58 of the can 20 by the anchor hole 70 and the connection hole 74 respectively receiving the anchor assembly 68 and case connection pin 66. The antenna assembly 25 is positioned for operational coupling with the electronics encased by the wall 21 of the can 20 by the feedthrough pin hole 72 receiving therein the antenna feedthrough 64.

Figure 4:
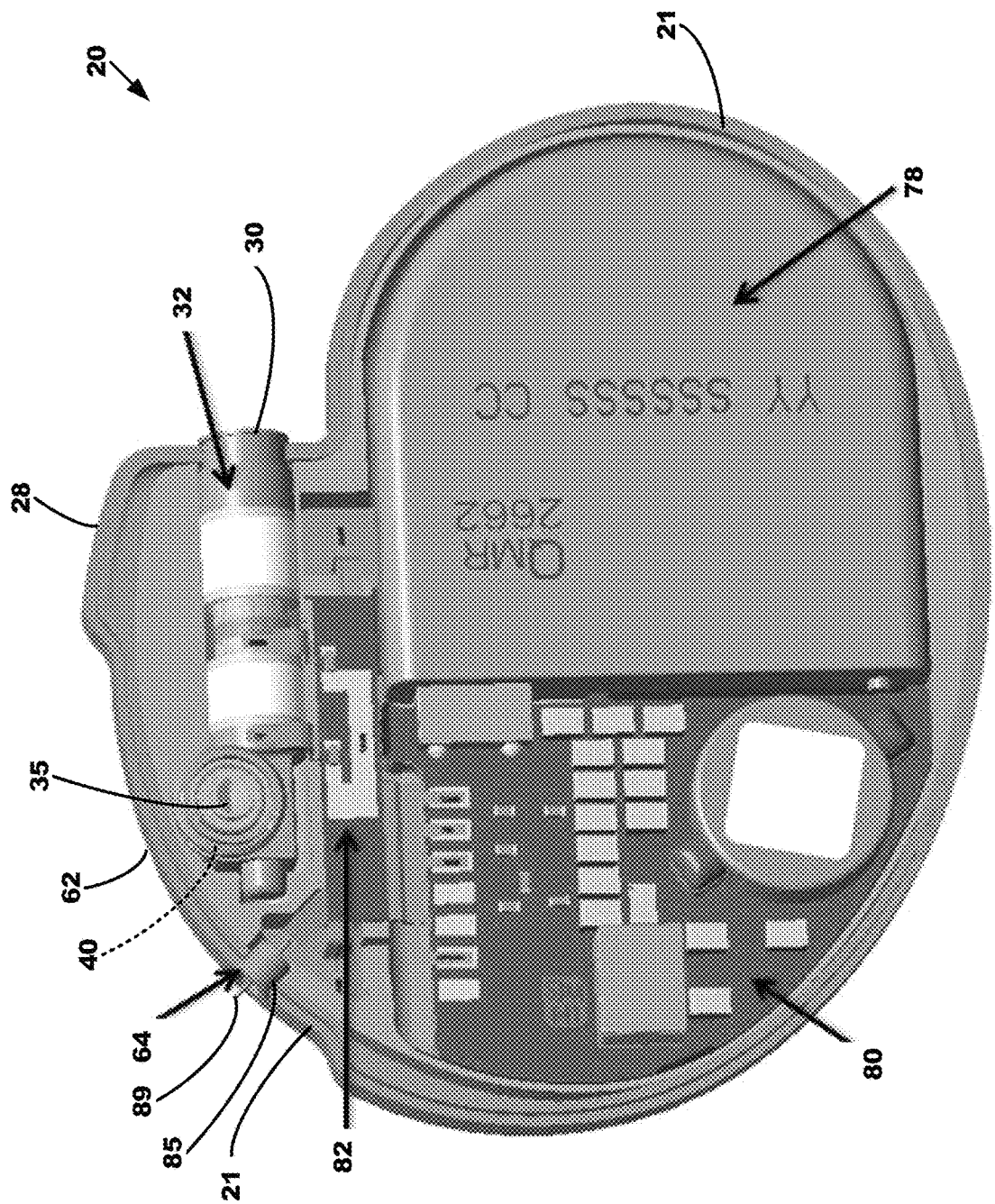
FIG. 4 is a cross sectional elevation of the metal can of the IMD as taken along section line 4-4 of FIG. 2.

As shown in FIG. 4, which is a cross sectional elevation of the can 20 of the IMD 10 as taken along section line 4-4 of FIG. 2, the can includes its shell or wall 21, the antenna feedthrough 64, a battery 78, the hermetic sealed lead connector assembly 32, a hybrid 80, and a rigid flex cable with EMI caps 82. Each of these electronic elements 64, 78, 32, 80 and 82 are electrically coupled as known in the art.

As can be understood from FIGS. 1-4, other than the antenna assembly 25 on the outside of the wall 21 of the can 20 and the feedthrough 64 that extends through the wall 21, all of the electrical components of the IMD 10 are contained within the confines of the all metal hermetic sealed wall 21 of the can 20.

Figure 5A:
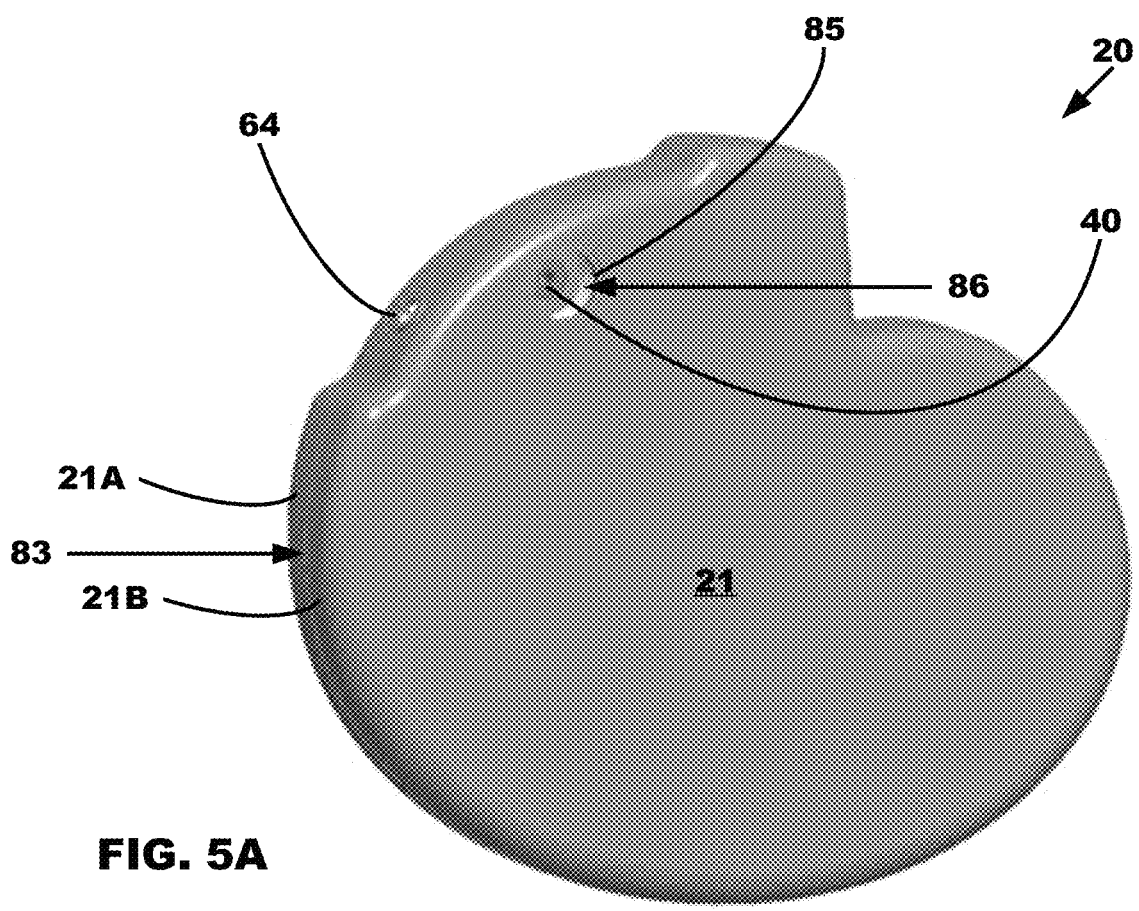
FIG. 5A is an isometric view of the can with the septum removed for clarity.
Figure 5B:
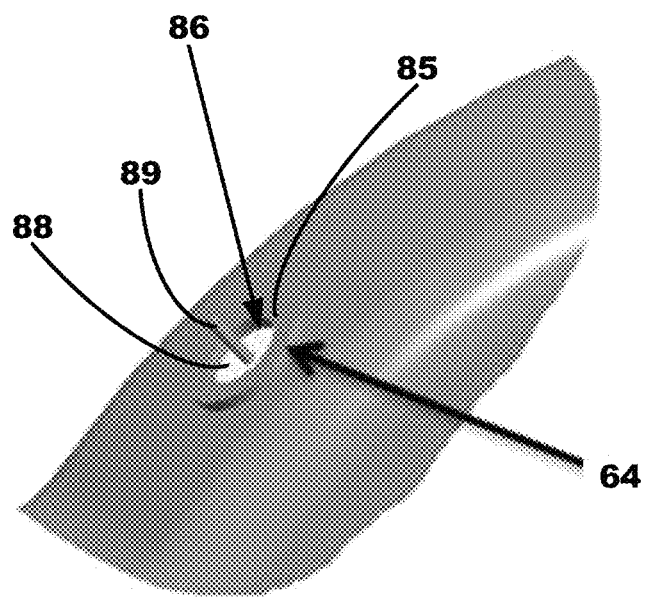
FIG. 5B is an enlarged view of the region of the can of FIG. 5A immediately adjacent the feedthrough.
Figure 6A:
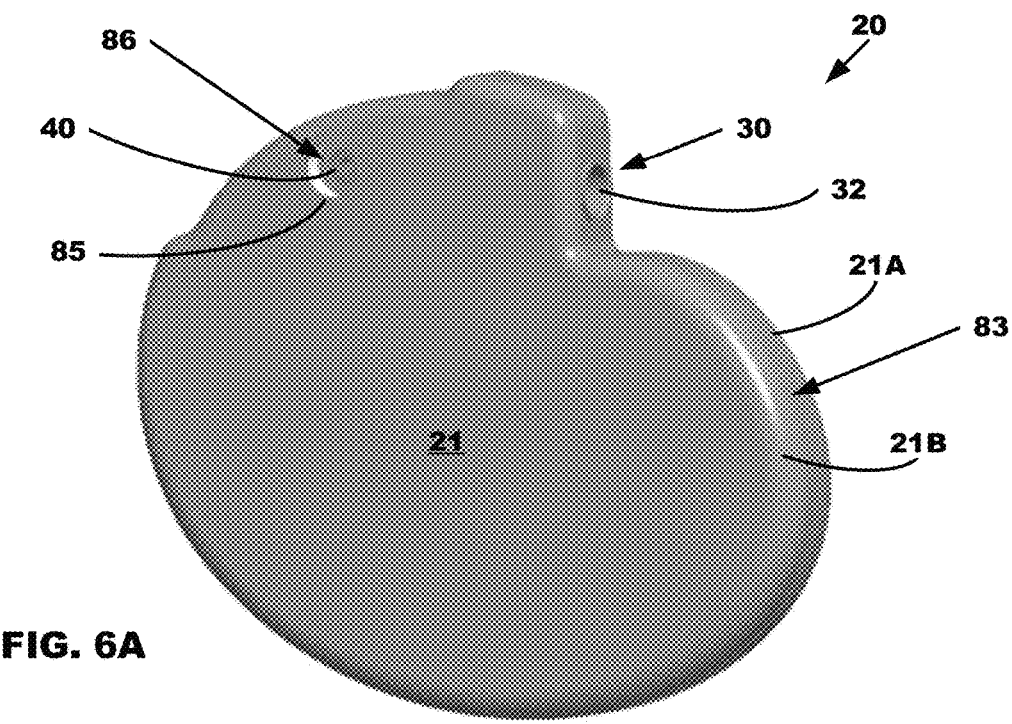
FIG. 6A is another isometric view of the can with the septum removed for clarity.
Figure 6B:
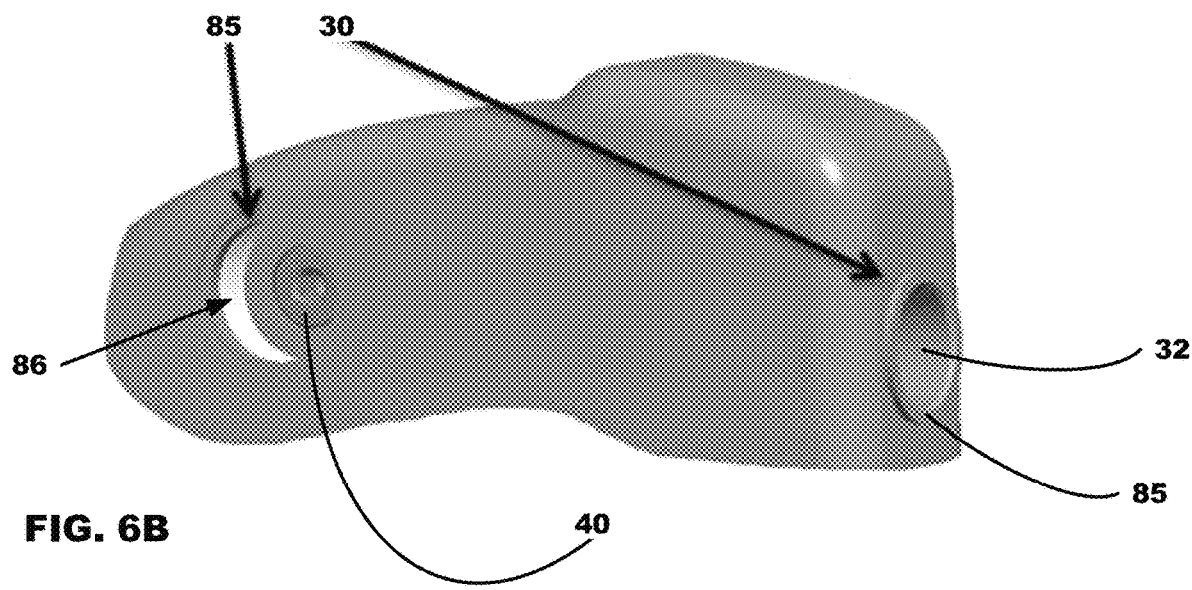
FIG. 6B is an enlarged region of the can of FIG. 6A immediately adjacent the setscrew assembly and the opening of the lead connector assembly.

FIGS. 5A and 6A are isometric views of the can 20 with the septum 35 removed for clarity. FIG. 5B is an enlarged view of the region of the can 20 immediately adjacent the feedthrough 64, and FIG. 6B is an enlarged region of the can 20 immediately adjacent the setscrew assembly 40 and the opening 30 of the lead connector assembly 32. As can be understood from FIGS. 5A-6B, in one embodiment, the wall 21 comes in two opposed halves 21A, 21B which may be welded along interfacing opposed edges to create a welded seam 83 to form the all metal hermetic sealed enclosure 21 of the can 20. Cylindrical cases 85 may be welded into the enclosure 21 to define hermetic sealed recesses 86 for the setscrew 40 and its septum 35, the feedthrough 64 and the lead connector assembly 32.

As shown in FIG. 5B, the cylindrical case 85 defines a hermetic sealed opening through the wall 21 for the feedthrough 64. The feedthrough 64 includes an electrical insulation portion 88 surrounding the conductor pin 89 of the feedthrough 64. The electrical insulation portion 88 may be a ceramic or other electrical insulation material.

Figure 7:
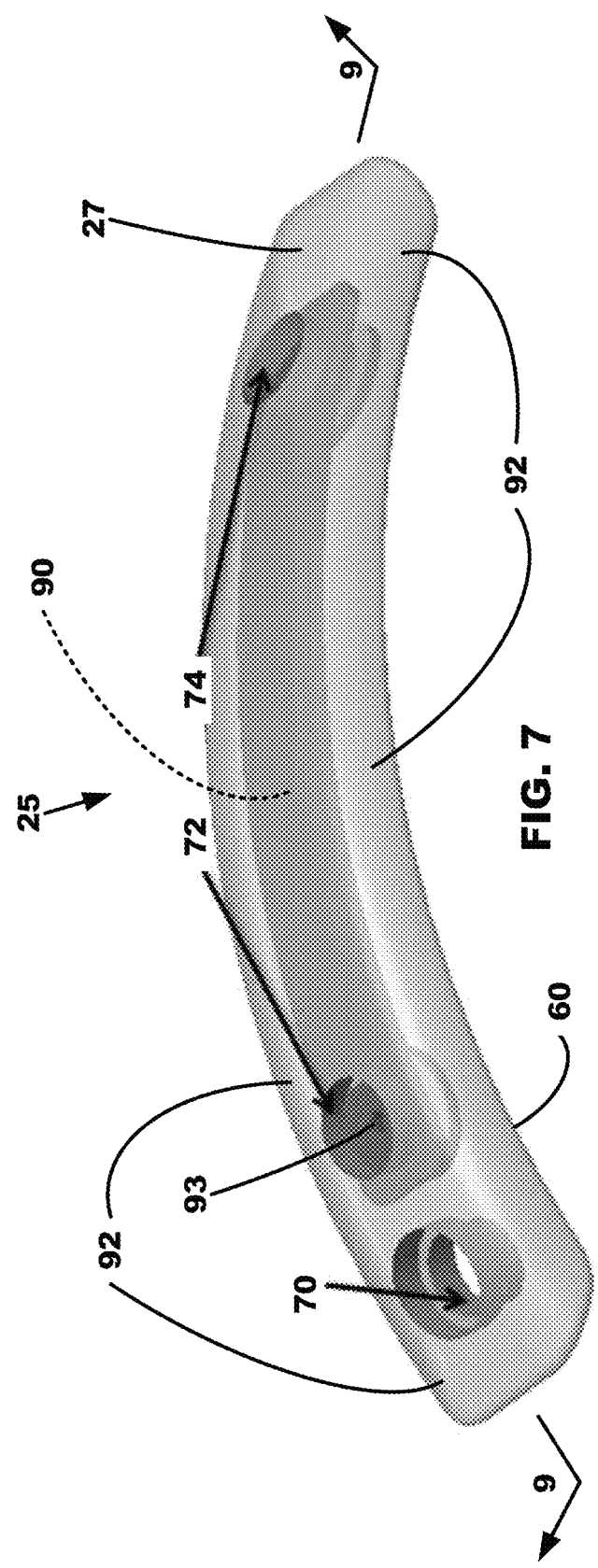
FIG. 7 is an enlarged isometric view of the antenna assembly of FIG. 3.

FIG. 7 is an enlarged isometric view of the antenna assembly 25 of FIG. 3. As indicated in FIG. 7, the antenna assembly 25 includes an antenna 90 and a polymer case 92 enclosing the antenna 90. In one embodiment, the antenna 90 is pre-molded into a bio-compatible thermoplastic case 92 prior to the antenna assembly 25 being mounted on the exterior of the can 20 as depicted in FIGS. 1 and 2. In other embodiments, the antenna 90 is welded in a spaced-apart configuration from the outer surface of the can 20 and then the bio-compatible thermoplastic case 92 is molded about the antenna 90 to form with the antenna 90 the antenna assembly 25. In either case, the thermoplastic case 92 may be tecothane or another bio-compatible plastic.

In one embodiment, the antenna 90 is pre-molded into a bio-compatible ceramic case 92 prior to the antenna assembly 25 being mounted on the exterior of the can 20 as depicted in FIGS. 1 and 2. In other embodiments, the antenna 90 is welded in a spaced-apart configuration from the outer surface of the can 20 and then the bio-compatible ceramic case 92 is molded about the antenna 90 to form with the antenna 90 the antenna assembly 25. In either case, the ceramic case 92 may be a biocompatible ceramic material known in the art.

Figure 8:
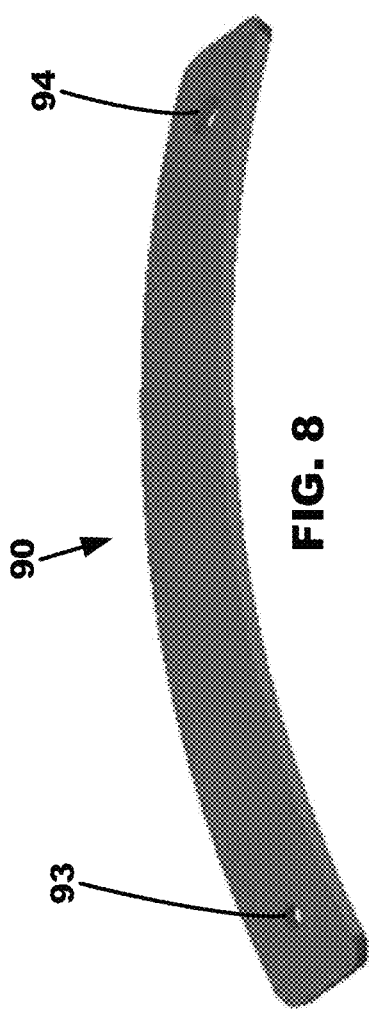
FIG. 8 is an isometric view of the antenna of the antenna assembly of FIG. 7 with the outer polymer case hidden to better illustrate the features of the antenna.

FIG. 8 is an isometric view of the antenna 90 of FIG. 7 with the outer polymer case 92 hidden to better illustrate the features of the antenna 90. As illustrated in FIG. 8, the antenna is a thin strip of metal (e.g., titanium, stainless steel, etc.) and has an arcuate shape that is complementary to the arcuate shape of the antenna assembly 25 as discussed above with respect to FIG. 3. The antenna 90 includes a feedthrough pin hole 93 for welding to the conductor pin 89 of the feedthrough 64, and a hole 94 for receiving and welding with the case connection pin 66.

As can be understood from FIG. 7, in one embodiment, the feedthrough pin hole 72 and connection hole 74 each provide respective holes in which the holes 93, 94 of the antenna 90 are generally centered.

Figure 9:
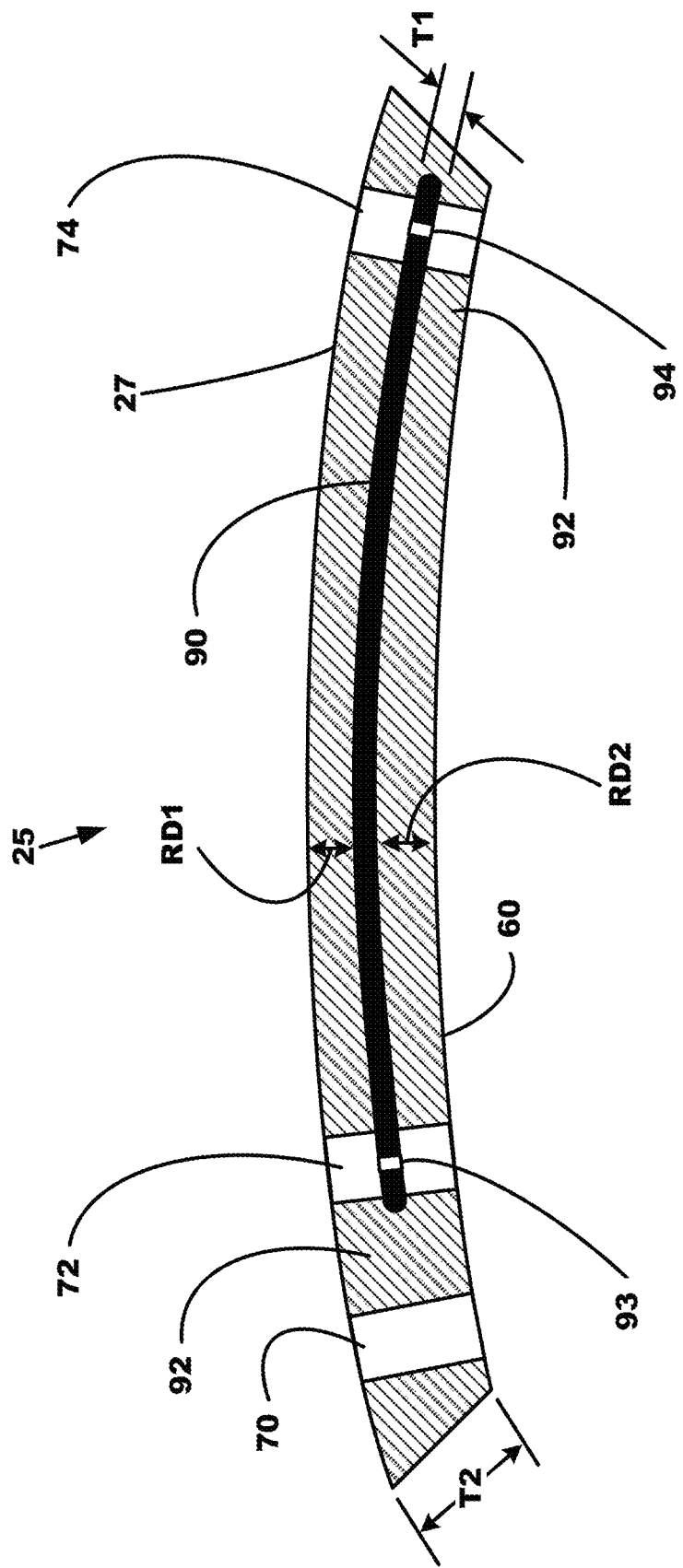
FIG. 9 is a longitudinal cross sectional side view of the antenna assembly as taken along section line 9-9 in FIG. 7.

FIG. 9 is a longitudinal cross sectional side view of the antenna assembly 25 as taken along section line 9-9 in FIG. 7. As can be understood from FIGS. 7 and 9, in one embodiment, the antenna 90 may have an end-to-end length of between approximately 0.7" and approximately 0.75", a side-to-side width of between approximately 0.06" and approximately 0.1", and a thickness T1 of between approximately 0.015" and approximately 0.03". The bio-compatible thermoplastic case 92 may have an end-to-end length of between approximately 0.9" and approximately 1", a side-to-side width of between approximately 0.10" and approximately 0.15", and a thickness T2 of between approximately 0.04" and approximately 0.1".

As depicted in FIG. 9, in one embodiment, the antenna 90 is generally centered within the confines of the thermoplastic case 92 side-to-side, and top-to-bottom, but not end-to-end on account of the location of the anchor hole 70. However, in some embodiments, the antenna 90 may also be generally centered within the confines of the thermoplastic case 92 end-to-end.

As indicated in FIG. 9, in one embodiment, a top surface of the antenna 90 may be recessed below the top surface 27 of the thermoplastic case 90 by a first recessed distance RD1 of between approximately 0.01" and approximately 0.03". Similarly, the bottom surface 60 of the thermoplastic case 90 may be recessed below the bottom surface of the antenna 90 by a second recessed distance RD2 of between approximately 0.02" and approximately 0.04". Thus, as can be understood from FIGS. 1, 3 and 9, when the antenna assembly 25 is mounted on the recessed region of the can 20 to form the overall IMD 10, the arcuate bottom surface of the antenna 90 is offset from the metal upper arcuate mating surface 62 of the recessed region of the can 20 by the second recessed distance RD2.

Figure 10A:
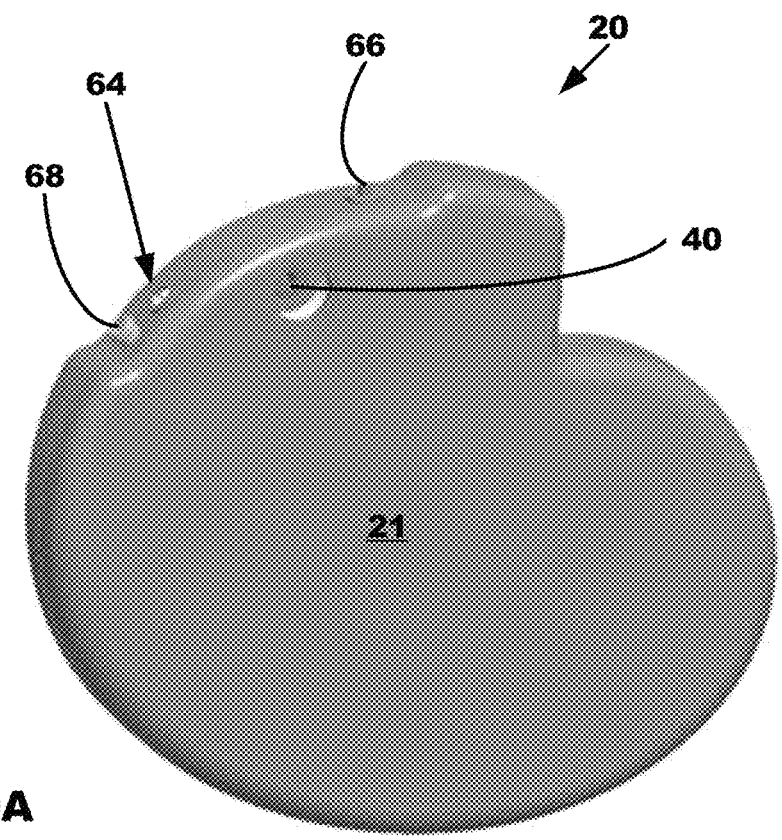
FIG. 10A is an isometric view of the can with its anchoring elements shown in the recessed region of the can.
Figure 10B:
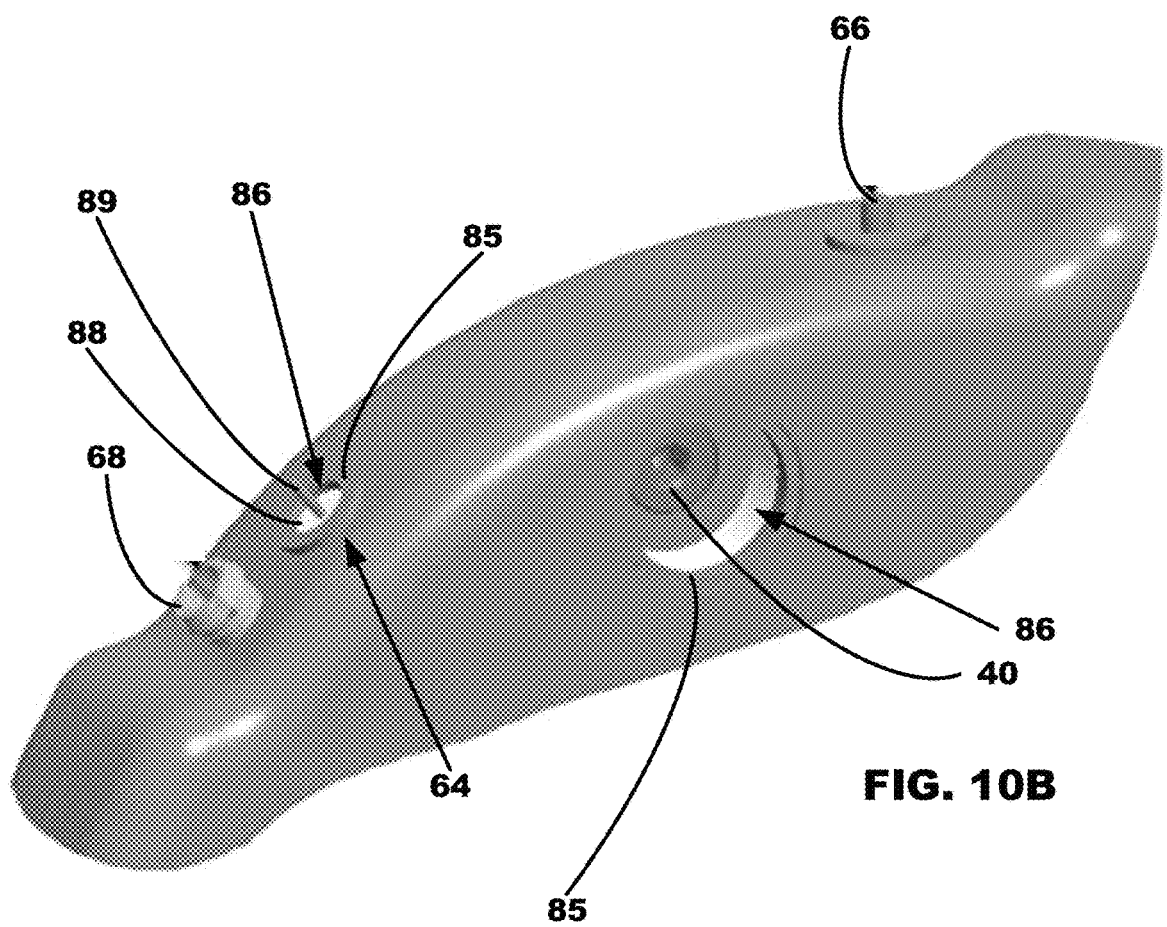
FIG. 10B is an enlarged view of the recessed region of the can in FIG. 10A.
Figure 11A:
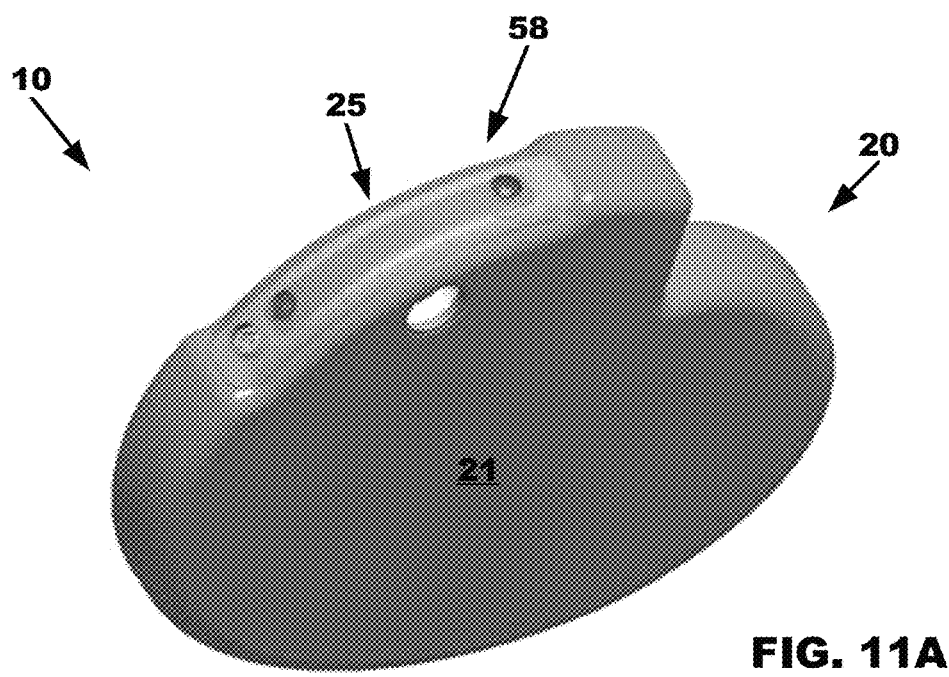
FIG. 11A is an isometric view of the IMD wherein the antenna assembly is mounted on the recessed region of the can of the IMD.
Figure 11B:
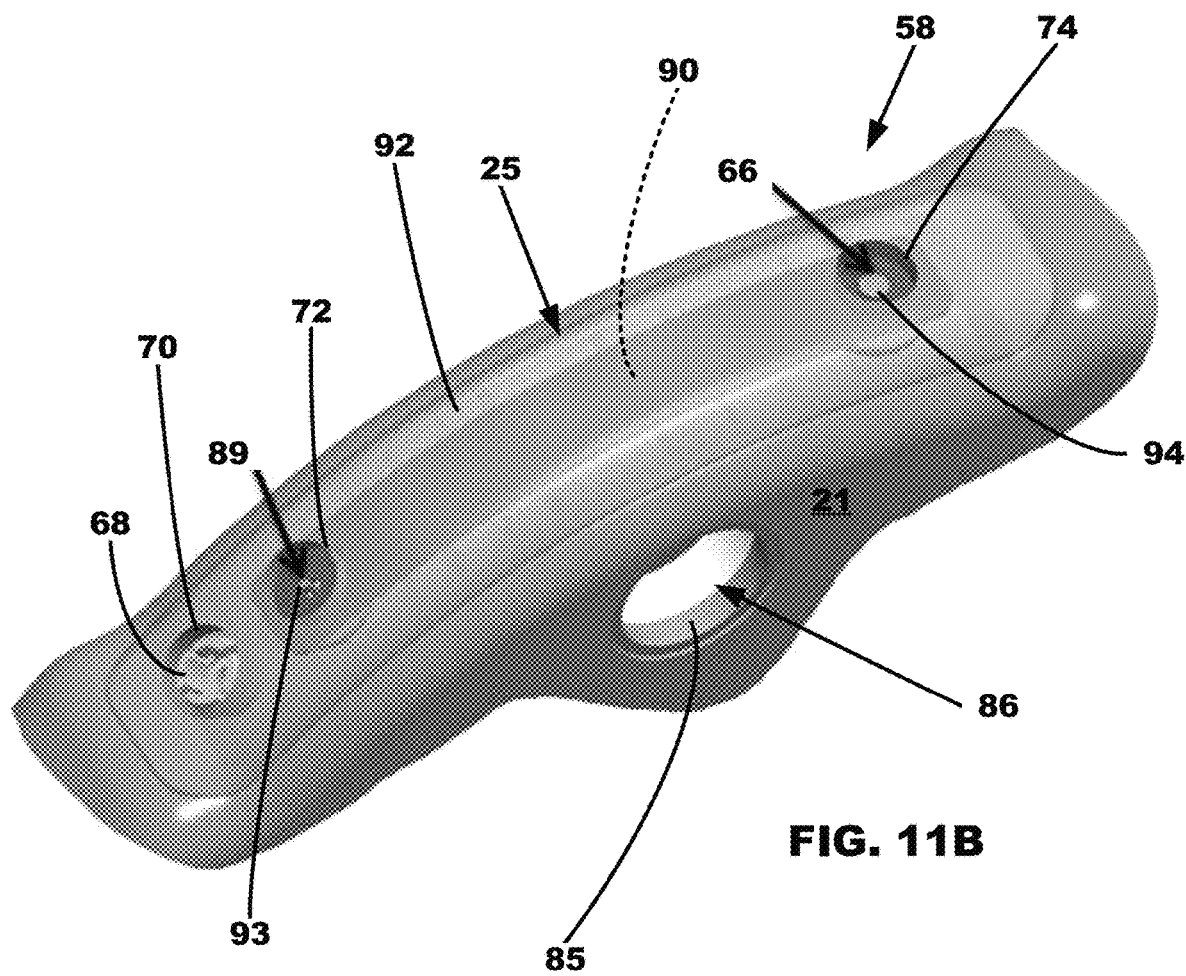
FIG. 11B is an enlarged view of the antenna region of the IMD of FIG. 11A.

FIGS. 10A and 10B are, respectively, another isometric view of the can 20 and an enlarged view of the recessed region 58 of the can 20 in FIG. 10B. FIGS. 11A and 11B are, respectively, an isometric view of the IMD 10 and an enlarged view of the antenna region of the IMD 10 in FIG. 11B. As can be understood from FIGS. 7, 9 and 10A-11B, in one embodiment, the feedthrough pin hole 72 and connection hole 74 each provide respective holes in which the holes 93, 94 of the antenna 90 can receive the corresponding pins 89, 66 of the recessed region 58 for welding connection. Similarly, the anchor hole 70 provides a hole through which the anchor assembly 68 may be inserted into the anchor hole 70 and welded to the wall 21 of the can 20.

Once the respective anchoring elements 66, 68, 89 are received in the respective openings 74, 70, 72 when the antenna assembly 25 is mounted on the can 25 in the recessed region 58 of the can 20, all three resulting welded locations operate to secure the antenna 90 and the antenna assembly 25 to the can 20, as shown in FIGS. 1, 11A and 11B. Once the welds are completed at each of these three locations between the pins 89, 66 and respective antenna holes 93, 94 and between the anchor assembly 68 and the can wall 21, the holes 70, 72, 74 in the antenna assembly 25 can be backfilled with a medical adhesive, epoxy or polymer material to provide a sealed and smooth contour along the top surface 27 of the antenna assembly 25. The setscrew septum 35 can then be installed in its recess, thereby completing the IMD 10 as it appears in FIG. 1.

As can be understood from FIGS. 1-4 and the discussion pertaining thereto, since all of the electronic components of the IMD 10 are essentially enclosed within the all metal hermetic sealed wall 21 of the can 20, the IMD 10 would otherwise only be capable of inductive telemetry communication absent the presence of the external antenna 90 enclosed in the polymer case 92 of the antenna assembly 25 mounted on the exterior of the wall 21 of the can 20. As a result of its exterior location, the antenna 90 facilitates RF/BLE telemetry communication for the IMD 10.

As can be understood from FIG. 12, which is the same view of the antenna assembly 25 of FIG. 9, except with the assembly 25 fully mounted on, and secured to, the all metal hermetic sealed wall 21 of the can 20, the antenna assembly 25 can be considered to form a patch antenna with the metal wall 21 of the can 20. In this case, the resulting patch antenna 25 would be a first plate (i.e., the antenna 90) offset from a second plate (i.e., the metal can wall 21) a distance RD2 (discussed above with respect to FIG. 9). The second plate 21 is below the first plate 90 and serves as the ground. The first plate 90 is above second plate 21 and serves as the signal or RF plate. In between the two plates 90, 21 is a dielectric material (i.e., the polymer case 92 of the antenna assembly 25).

At Bluetooth™ frequencies, the patch antenna can be designed to take up a smaller cross sectional area than other antennas such as the monopole and loop antennas. The signal is fed to the top plate 90 via the RF conductor (i.e., the feedthrough pin 89), and grounding is provided via the grounding conductor (i.e., the case connection pin 66).

In addition to being smaller than other antennas, it is also easier to tune the critical parameters of a patch antenna such as frequency, bandwidth, and impedance. Because the patch forms a capacitor with the can surface, the dimensions, shape, and length of the patch plate determine those critical parameters.

As stated before, a patch antenna is formed between the first plate 90 and the metal surface 21 of the can 20, with the metal surface acting as a grounding plate when the plate 90 receives a signal from the electronics of the can 20. The polymer material 92 forming the polymer case 92 of the antenna assembly 25 acts as the dielectric between the two electrically conductive surfaces of the patch antenna. The polymer material can be in the form of a thermoset polymer (e.g., epoxy) or an injectable polymer such as, for example, polyurethane, tecothane, pellethane, bionate, silicone, acrylic, or etc.

In some embodiments, instead of a the dielectric case 92 being a formed of a polymer material 92 to form a polymer case 92, the dielectric case 92 will be formed of a ceramic material 92 to form a ceramic case 92. Use of a ceramic material in place of a polymer material for the dielectric case 92 may provide advantages in the overall size of the antenna assembly 25, which may be smaller with the ceramic material as compared to what is possible via the use of a polymer material.

In one embodiment, the implantable medical device 20 may be designed and manufactured as follows. A manufacturer would identify a resonance frequency for communications between an implantable medical device and an exterior device. Such an implantable medical device may include a housing assembly having a metal surface and enclosing electronics. The metal surface may have a feedthrough opening, and may be electrically connected to a feedthrough flange containing the feedthrough opening. A patch antenna of the implantable medical device may include a plate electrically connected to the electronics via a pin extending through the feedthrough opening. The metal surface of the housing (and any electrically connected feedthrough flange) may form a ground plate for the patch antenna, with the result being that the entire surface of the housing can be considered the ground plate. A polymer (or ceramic) material may be formed about the antenna 90 to enclose the antenna 90 and form the antenna assembly 25. A polymer (or ceramic) material may form the dielectric between the surfaces of the patch antenna. The polymer (or ceramic) material in some embodiments is the polymer (or ceramic) material that forms the polymer (or ceramic) case 92 (i.e., dielectric case 92) of the antenna assembly 25 enclosing the antenna 90. With such an implantable medical device, the manufacturer would then modify, based on the resonance frequency, at least one of a plate size of the plate 90, a shape of the plate 90, a distance between the plate 90 and the metal surface 21, a location of the feedthrough opening, or a length of the feedthrough pin 89. The modifying may alter at least one of a capacitance or an inductance associated with the patch antenna. The polymer (or ceramic) material 92 may be modified based on the resonance frequency. The plate 90 of the patch antenna may be shorted to the metal surface by a second pin 66 at another location of the plate away from the feedthrough pin 89 (such as an opposite edge of the RF plate).

The patch antenna can, in various configurations, communicate in a Bluetooth™ frequency band, including 2.40 to 2.48 GHz. The patch antenna can have a planar orientation which is parallel to the metal surface of the housing assembly. The patch antenna can have a single ground plate. Similarly, the patch antenna can be shorted, such that the grounding pin is on another location or portion of the RF plate away from the RF pin providing a signal to the RF plate. A shorted patch antenna is advantageous in that it allows for the antenna to be half the size of a non-shorted patch antenna.

Once the antenna has the desired resonance frequency, the dielectric material 92 can be applied such that the patch antenna is covered by the dielectric material 92, which may be a polymer, ceramic or other dielectric material. The dielectric material 92 can act as a dielectric for the patch antenna. Because the dielectric affects the antenna performance, the choice of dielectric material 92 used for the antenna assembly 25 can be made based on the resonance frequency.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A method of manufacturing an implantable medical device (IMD), the method comprising:
    positioning an antenna within a recessed outer region of a housing of the IMD so that the antenna extends along a recessed surface of a metal wall of the housing in a spaced apart manner, the metal wall defining a hermetic sealed compartment in which electronics of the IMD are located, and a feedthrough extending through the recessed surface such that a first portion of the feedthrough is disposed on a first side of the metal wall and within the hermetic sealed compartment and a second portion of the feedthrough is disposed on a second side of the recessed surface external the hermetic sealed compartment; and
    electrically connecting the antenna via an RF conductor of the feedthrough to the electronics located within the hermetic sealed housing;
    wherein the antenna is encased in a dielectric material that fills a space between the antenna and the metal wall.

2. The method of claim 1, wherein the dielectric material includes at least one of a thermosetting polymer, an epoxy, thermoplastic, polyurethane, tecothane, pellethane, silicone, acrylic, bionate, or ceramic.

3. The method of claim 1, wherein the antenna has an end-to-end length of between approximately 0.7" and approximately 0.75", a side-to-side width of between approximately 0.06" and approximately 0.1", and a thickness of between approximately 0.015" and approximately 0.03".

4. The method of claim 3, wherein the metal wall is spaced-apart from a bottom surface of the antenna by between approximately 0.02" and approximately 0.04".

5. The method of claim 1, wherein:
    the dielectric material and the antenna encased therein form an antenna assembly;
    the antenna assembly is disposed in the recessed outer region and extends along the recessed surface in a spaced-apart manner from the recessed surface; and
    the dielectric material occupies a space between the antenna and the recessed surface.

6. The method of claim 5, wherein the recessed surface forms a ground plate for the antenna.

7. The method of claim 5, wherein a case connection pin electrically connects the antenna to the recessed surface.

8. The method of claim 5, wherein a case connection pin electrically connects the antenna to the recessed surface and the case connection pin and the RF conductor have electrical connections with the antenna at opposite areas of the antenna.

9. The method of claim 5, wherein the antenna and the recessed surface have matching arcuate configurations such that spacing between the antenna and the recessed surface is consistent along an end-to-end length of the antenna.

10. The method of claim 5, wherein an anchor couples the antenna assembly to the recessed surface.

11. The method of claim 5, wherein a case connection pin electrically connects the antenna to the recessed surface, wherein an anchor couples the antenna assembly to the recessed surface, and wherein the case connection pin and the anchor are disposed at opposite ends of the antenna assembly.

12. The method of claim 5, wherein a case connection pin electrically connects the antenna to the recessed surface, wherein an anchor couples the antenna assembly to the recessed surface, wherein the case connection pin and the anchor are disposed at opposite ends of the antenna assembly, and wherein the RF conductor is located between the case connection pin and the anchor.

13. The method of claim 1, wherein a lead connector assembly is also located within the hermetic sealed compartment.

14. The method of claim 1, further comprising:
    electrically connecting the antenna to the recessed surface of the metal wall of the housing via a case connection pin.

15. The method of claim 14, wherein the dielectric material and the antenna encased therein form an antenna assembly applied as a unit to the metal wall when the antenna is electrically connected to the metal wall via the case connection pin.

16. The method of claim 14, wherein the dielectric material is applied about the antenna subsequent to the antenna being electrically connected to the metal wall via the case connection pin.

17. The method of claim 14, wherein the recessed surface of the metal wall forms a ground plate for the antenna.

18. The method of claim 17, wherein the antenna and the recessed surface of the metal wall, which are separated from one another by the dielectric material, form a patch antenna.

\* \* \* \* \*